(12) United States Patent
Kobayashi et al.

(10) Patent No.: US 6,471,691 B1
(45) Date of Patent: *Oct. 29, 2002

(54) OPHTHALMIC TREATMENT APPARATUS

(75) Inventors: Koji Kobayashi, Hamamatsu (JP); Toru Hirano, Hamamatsu (JP); Shigeru Sakamoto, Hamamatsu (JP); Hideaki Niwa, Chofu (JP); Akira Obana, Myojin 3-2-5, Oji-cho, Kitakatsuragi-gun, Nara 636-0022 (JP); Tokuhiko Miki, Akasakadi 5-11-12, Sakai City, Osaka 590-0144 (JP)

(73) Assignees: Kowa Company Ltd. (JP); Hamamatsu Photonics K.K. (JP); Akira Obana (JP); Tokuhiko Miki (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/378,211

(22) Filed: Aug. 19, 1999

(30) Foreign Application Priority Data

Aug. 20, 1998 (JP) .......................................... 10-233660

(51) Int. Cl.[7] ............................................... A61B 18/20

(52) U.S. Cl. ................................ 606/4; 606/10; 606/13; 606/17; 604/20; 607/89; 600/473

(58) Field of Search ........................ 606/4–13; 604/19, 604/20; 607/88–96; 351/204, 206, 221; 600/473

(56) References Cited

U.S. PATENT DOCUMENTS

| 4,579,430 A | * | 4/1986 | Bille | 606/12 |
| 4,838,679 A | * | 6/1989 | Bille | 351/221 |
| 6,128,524 A | * | 10/2000 | Yoneya et al. | 606/4 |

* cited by examiner

*Primary Examiner*—David M. Shay
(74) *Attorney, Agent, or Firm*—Adams & Wilks

(57) ABSTRACT

An ophthalmic treatment apparatus uses therapy and diagnostic laser light sources whose beams are deflected two-dimensionally via an optical deflector and a galvanomirror and directed on the eye fundus to produce a fundus image on a display monitor. A photosensitive substance that accumulates specifically in neovascular regions is administered to the patient to define the region where the neovascular tissues are located. When the region is to be treated, the therapy laser light source is activated and its intensity is amplified by a controller and a driver for driving a light modulator. This arrangement assures a reliable definition of the affected region and enables only the neovascular tissues to be destroyed or sealed off because the laser intensity can be amplified at the region concerned.

30 Claims, 4 Drawing Sheets

OPHTHALMIC TREATMENT APPARATUS

BACKGROUND OF THE INVENTION

1. Field of the Invention

The present invention relates to an ophthalmic treatment apparatus, and more particularly to an ophthalmic treatment apparatus that uses laser light.

2. Description of the Prior Art

The manifestation of neovascular tissues in retinal lesions or degeneration in the eye fundus can indicate the progress of a disease. Various treatment methods have been tried for removing neovascular tissues. These include surgery to remove the neovascular tissues, the use of laser coagulators, and, more recently, treatment using the drug Interferon, and radiation treatment. The problem with surgery is that it is an invasive method that also damages normal tissue, leaving after-effects such as a deterioration in visual acuity. The success rate with treatments using drugs or radiation cannot be described as very high, either, and there are concerns about after-effects and side effects.

At present the laser coagulator method is considered the surest, but the heat of the laser beam scorching the retina can result in a loss of function by cells in the coagulated portion, thereby degrading vision. That is, the problem with the laser coagulation method is that technically it is virtually impossible to coagulate just the neovascular tissues without at the same time destroying normal cells in the vicinity of the vascularized region.

To address this problem, the present applicants filed a joint application for a new ophthalmic treatment apparatus that utilizes a photochemical reaction between radiated light and a photosensitive substance (JP-A 9-173376). That apparatus employs a laser projector that utilizes a fundus camera optical system. The patient is administered a photosensitive substance or photosensitizer that accumulates specifically in the neovascular tissues. Then, when the neovascular portion fluoresces, the laser beam is focused on the fluorescing portion to thereby selectively destroy or seal the neovascular tissues.

However, although the above ophthalmic treatment apparatus is based on the photochemical reaction principle, the laser beam projected via the fundus camera optical system irradiates the eye fundus with a certain degree of divergence. As a result, it was found that because the tissues around the neovascular tissues in the fundus were also irradiated by the laser, there was also a possibility of impairment of the surrounding normal tissue. While fluorography using contrast medium is an effective way of determining the position of neovascular tissues in an affected region, some such fundus-camera based systems do not have the sufficient fluorographic resolving power or contrast required for diagnostic purposes, and real-time close-up observation of the affected area using a safe light-intensity level is also difficult.

An object of the present invention is to provide an ophthalmic treatment apparatus that enables real-time close-up observation of the eye fundus and simultaneously enables irradiation with the therapy laser beam, thereby making it possible to treat neovascular tissue lesions without affecting normal cells and go minimizing any reoccurrence of the condition.

SUMMARY OF THE INVENTION

In accordance with the present invention, the above object is attained by an ophthalmic treatment apparatus in which a laser beam from a laser light source is projected via an optical system onto an eye fundus of a patient's eye for treatment thereof, comprising a laser light source that generates a laser beam having a predetermined wavelength, optical scanning means for deflecting the laser beam from the laser light source at a predetermined frequency to scan the eye fundus therewith, and output means for detecting an intensity of reflected light and fluorescent light from the eye fundus to output an image of the eye fundus based on the scanning by the optical scanning means, wherein a photosensitive substance that accumulates specifically in neovascular tissues is administered to the patient to define a region of the eye fundus including the neovascular tissue portion based on the eye fundus image, and the region thus defined is irradiated by the laser beam from the laser light source to cause a photochemical reaction between the photosensitive substance and the laser beam, thereby destroying or sealing off the neovascular tissues concerned.

The above object is also attained by an ophthalmic treatment apparatus in which a laser beam from a laser light source is projected via an optical system onto an eye fundus of a patient's eye for treatment thereof, comprising a laser light source that generates a laser beam having a predetermined wavelength, optical scanning means for deflecting the laser beam from the laser light source at a predetermined frequency to scan the eye fundus therewith, output means for detecting an intensity of reflected light and fluorescent light from the eye fundus to output an image of the eye fundus based on the scanning by the optical scanning means, means for defining a region of the eye fundus including a neovascular tissue portion based on the eye fundus image obtained after a photosensitive substance that accumulates specifically in neovascular tissues has been administered to the patient, and means for amplifying a laser beam intensity during scanning of the defined region by the laser beam.

The basis of the invention is that after a photosensitive substance that accumulates specifically in the neovascular tissues has been administered to the patient and the photosensitive substance has accumulated in the neovascular tissues, a scanning laser ophthalmoscope is used to project a therapy laser beam at the region concerned. In accordance with this invention a scanning laser ophthalmoscope is combined with a laser system that outputs a high-power laser treatment beam. This makes it possible to accurately focus the therapy laser beam on the neovascular tissues while at the same time observing a close-up image of the eye fundus on a TV monitor. Thus, compared to a conventional eye fundus camera system, the system of this invention makes it possible to reduce the influence of the laser beam on the surrounding tissues, and thereby enables the neovascular lesion to be treated easily and reliably.

Further features of the invention, its nature and various advantages will become more apparent from the accompanying drawings and following detailed description of the invention.

DESCRIPTION OF THE PREFERRED EMBODIMENT

Figure 1:
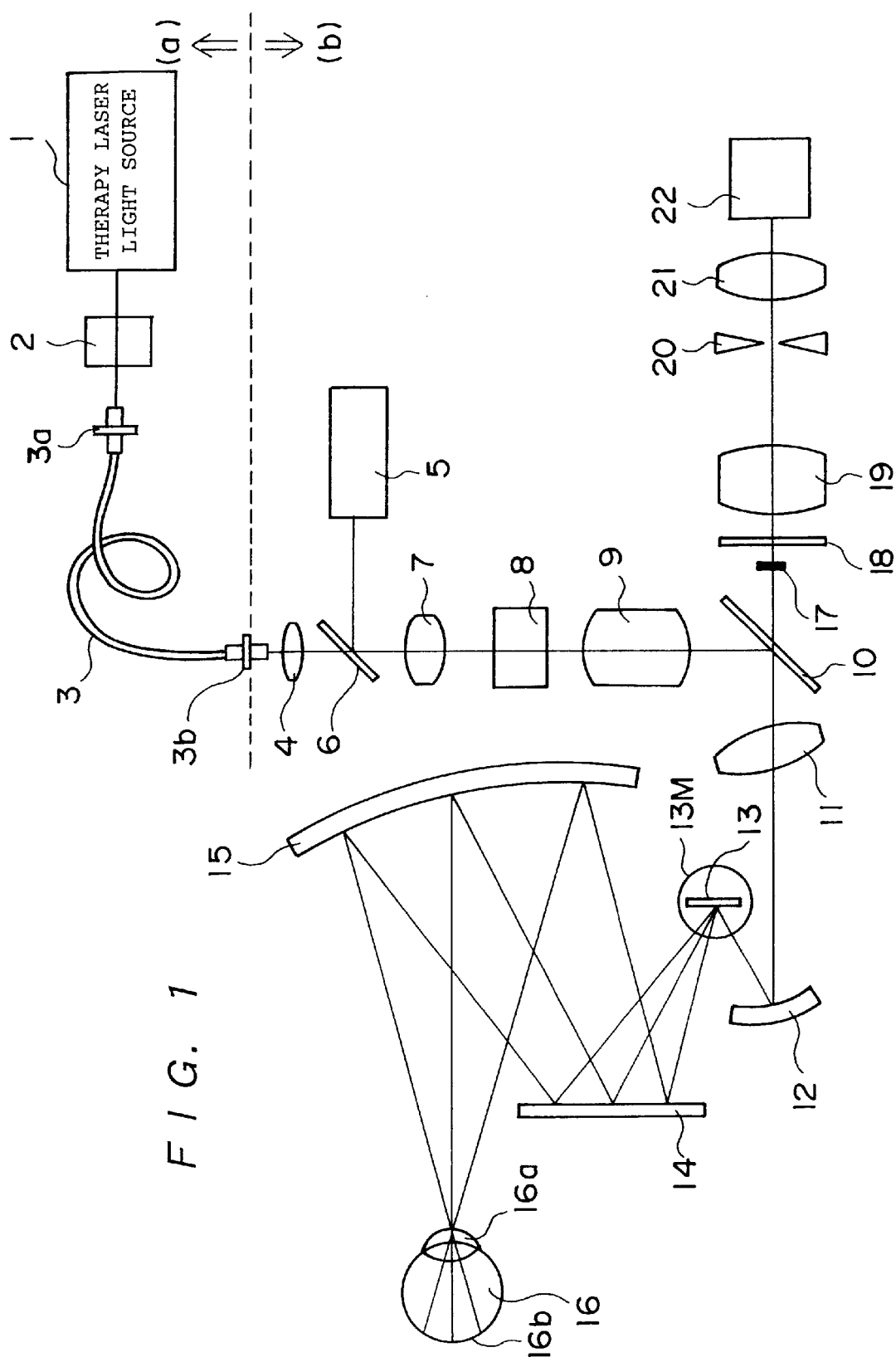
FIG. 1 is a diagram showing the optical system of an ophthalmic treatment apparatus of the invention.

FIG. 1 shows the general arrangement of an ophthalmic treatment apparatus of this invention. In FIG. 1, reference numeral 1 denotes a semiconductor laser light source or laser diode that generates a high-power, therapy red-light laser light beam with a wavelength of, for example, 670 nm and a power of several hundred milliwatts. The therapy laser light beam from the laser light source 1 passes through a light modulator 2 and can be adjusted to any desired intensity. From the light modulator 2, the laser beam passes through optical connector 3a and into optical fiber 3, passes through the optical fiber 3 and is emitted from the other end, via optical connector 3b. The optical fiber 3 is for example a multimode optical fiber having a core diameter of from 50 to 200 μm, able to efficiently transmit the laser beam without loss. In FIG. 1, the therapy laser light source section (a) and a scanning laser ophthalmoscope (b), described below, are linked by the optical fiber 3, with a dashed line indicating the division therebetween.

The laser beam exiting the optical fiber 3 is collimated by lens 4 and the optical path thereof merged with that of the laser beam from diagnostic low-power laser light source 5 by beam-splitter 6. The laser light source 5 is a small semiconductor laser that generates a beam of several milliwatts and the same wavelength as the laser light source 1 for fluorescent diagnostic purposes. Laser light sources 1 and 5 can be switched on and off independently to allow a diagnostic or therapy beam to be selected as required. The beam-splitter 6 has, for example, a reflectance of 30% and a transmittance of 70% for transmitting the therapy laser beam with minimal loss.

The diagnostic laser light source can be configured as a plurality of laser light sources of different wavelengths whose optical paths can be merged by a dichroic mirror or the like. For example, an arrangement may be used comprising a laser light source that produces visible light of wavelength 670 nm for forming eye fundus images or fluorographic images, and a laser light source that produces light of wavelength 780 nm for forming eye fundus images using infrared light or infrared fluorescent light, with the light beams being merged into a composite beam. For simplicity, however, FIG. 1 only shows the one diagnostic laser light source 5.

The light beams merged by the beam-splitter 6 pass through lens 7, correcting the shape of the composite beam to a square shape. The beam then impinges on the incident opening of an optical deflector 8. The optical deflector 8 can be an acousto-optic deflector (AOD) formed of an optical crystal such as tellurium dioxide that in accordance with the diffraction principle uses ultrasound waves to effect high-speed scanning of the laser light from the laser light source 1 and/or the laser light source 5. A scanning frequency of 15.75 kHz is used, which is compatible with the horizontal scanning of a standard NTSC TV signal. Instead of an AOD, a resonant frequency type high-speed deflecting mirror or a rotating polygon mirror or the like can be used to effect the high-speed scanning. The description herein is made with reference to the optical deflector 8 of FIG. 1 that is an AOD. The laser light beam deflected one-dimensionally at high speed passes through a lens unit 9 that includes a plurality of cylindrical lenses and the like, correcting the beam to a round shape.

The laser light beam emitted by the lens unit 9 is reflected by a beam-splitter 10 through a relay lens 11 and a concave mirror 12 and is reflected and deflected by a mirror (galvanomirror) 13 attached to a galvanometer 13M. The relay lens 11 is set at a slight angle to the optical axis to prevent light reflected at the lens' surface from entering the detection system and giving rise to flare. The galvanomirror 13 is for deflecting the light beam vertically at a frequency such as 60 Hz that is compatible with the vertical scanning signal of a standard TV. Thus, the galvanomirror 13 deflects the light beam at a low speed perpendicularly to the direction of the scanning by the optical deflector 8. Rasters formed by the laser beam being deflected in the two dimensions by the optical deflector 8 and galvanomirror 13 are reflected by a plane mirror 14 and a concave mirror 15, pass through the pupil 16a of the subject eye 16 and impinge on the eye fundus 16b.

Reflected or fluorescent light from the eye fundus 16b is guided back through the concave mirror 15, plane mirror 14, galvanomirror 13, concave mirror 12, relay lens 11 and beam-splitter 10. To remove corneal reflections, reflected or fluorescent light from the eye is passed through a black spot 17 located behind the beam-splitter 10, and is then passed through a filter 18, lens 19, confocal aperture 20 and lens 21, and is detected by a high-sensitivity photodetector 22 such as a photomultiplier or avalanche photodiode. The filter 18 is a sharp-cut filter for detecting fluorescent light of around 700 nm produced when a 670 nm laser is used to excite a photosensitive substance such as an oncotropic porphyrin-based chemical substance, for example, ATX-S10 (produced by Toyo Hakka Kogyo), that is intravenously administered to the patient. The confocal aperture 20 serves to eliminate the effect of undesired scattered light in the optical system including the eye, and a high-contrast video signal at a video rate for displaying the eye fundus images is produced from the photodetector 22.

Figure 2:
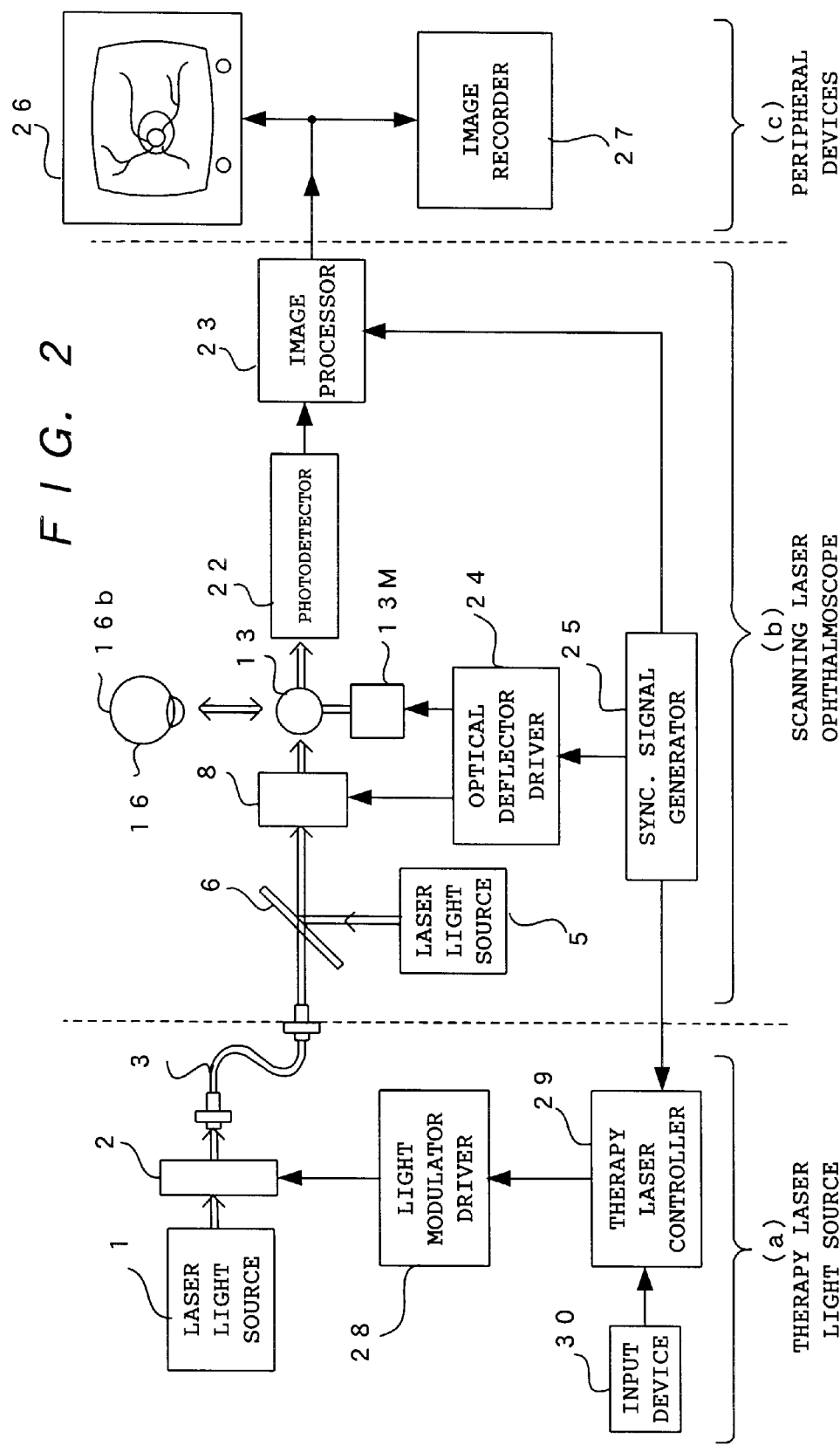
FIG. 2 is a block diagram showing the electrical system of an ophthalmic treatment apparatus of the invention.

FIG. 2 shows the electrical control system of the ophthalmic treatment apparatus. The laser beam from the therapy high-power semiconductor laser light source 1 is intensity-modulated by the light modulator 2 and guided by the optical fiber 3 to the optical system of the scanning laser ophthalmoscope, which has already been described in connection with FIG. 1. At the beam-splitter 6, the therapy laser beam exiting the optical fiber 3 is merged with the laser beam from the diagnostic, low-power laser light source 5, and the ultrasonic optical deflector 8 and galvanomirror 13 deflect the beams in two dimensions on the eye fundus 16b to scan the same.

The intensity of light reflected by the eye fundus 16b, or of the fluorescent light detected after administration of the photosensitive substance, is detected by the photodetector 22 and its image is processed by an image processor 23. The deflection operation of the optical deflector 8 and galvanomirror 13 constituting the scanning optical system is controlled by an optical deflector driver 24 in accordance with a synchronizing signal received from a synchronization signal generator 25. If 15.75 kHz and 60 Hz are the frequencies selected for the scanning by the optical deflector 8 and galvanomirror 13, the signals output by the image processor 23 are video signals compatible with the TV scanning system of the NTSC standard format. Therefore, the signals output by the image processor 23 can be supplied to a TV monitor or other such image display device 26 shown as part of the peripheral device section (c) to thereby enable the images of the eye fundus to be displayed thereon in real-time. It is also of course possible, if required, for the video signal to be supplied to an image recording apparatus 27 such as a VCR or computer to record eye fundus images as moving or still images.

The light modulator 2 used to modulate the intensity of the laser beam from the high power therapy laser light source 1 is controlled by a light modulator driver 28 and a therapy laser controller 29. The intensity and location of the therapy laser beam are controlled by an input device 30 such as a mouse or keyboard. That is, when the eye fundus is being diagnostically examined following the intravenous administration of the photosensitive substance, the high-power therapy laser light source 1 is switched off and the laser beam from the low-power diagnostic laser light source 5 is used to observe the eye fundus images and fluorescent images resulting from the photosensitive substance, to thereby define the location of neovascular tissues developed at the site of the affliction in the eye fundus. The input device 30 is then used to specify on the screen the neovascular tissue region that needs to be treated and to store the coordinates of its location in a memory (not shown) in the therapy laser controller 29. The therapy laser light source 1 is then energized and, based on the visual image thus obtained, the therapy laser controller 29 increases the intensity of the laser beam from the laser light source 1 at the specified coordinates on the eye fundus scanned by the optical deflector 8 and galvanomirror 13.

Figure 3:
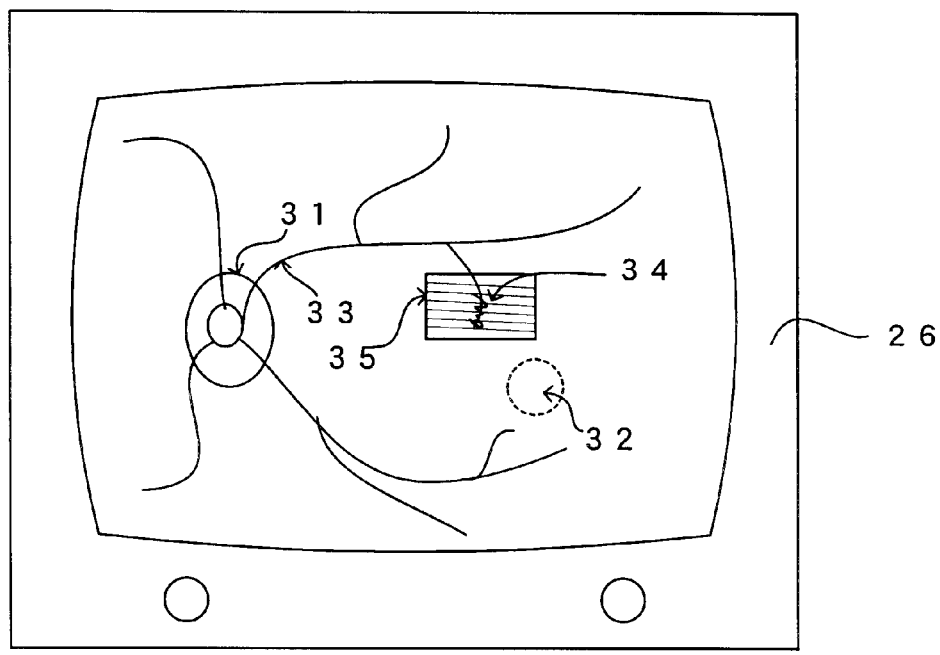
FIG. 3 is an illustrative view showing an eye fundus image shown on a monitor.

FIG. 3 illustratively shows the control of the laser beam in the eye fundus on a monitor screen. In FIG. 3, the image display device (TV monitor) 26 is used to provide a real-time display of the eye fundus images produced for observational purposes by scanning the fundus with the diagnostic laser beam from the low-power laser light source 5 described with reference to FIGS. 1 and 2. In FIG. 3, reference numeral 31 denotes the papilla portion of the fundus, and 32 the macula retinae. A thick blood vessel 33 is shown extending from the papilla portion 31 to the macula retinae 32. In this example, the eye fundus disease has given rise to neovascular tissues at a location 34, which is taken as the treatment target.

The ophthalmic treatment apparatus is used to observe eye fundus images following the administration of the photosensitive substance. The therapy laser light source 1 is then controlled in such a way that its laser beam is intensified at scanning region 35 to cause a photochemical reaction between the laser light and the photosensitive substance that has accumulated in the neovascular tissues, enabling them to be effectively destroyed or sealed off. The scanning region 35 is shown as being rectangular in shape, but it can readily be set to be oval or any other desired shape by computer control in the therapy laser controller 29 (FIG. 2). The critical portions in the vicinity of the macula retinae can be treated by using the TV monitor to view the eye fundus in close-up while adjusting the irradiation of the therapy laser beam to the minimum surface area required. Thus, in conjunction with the accumulation of the photosensitive substance at the neovascular tissues, it is possible to carry out the treatment while minimizing the influence on the normal tissue cells of the eye fundus.

Figure 4:
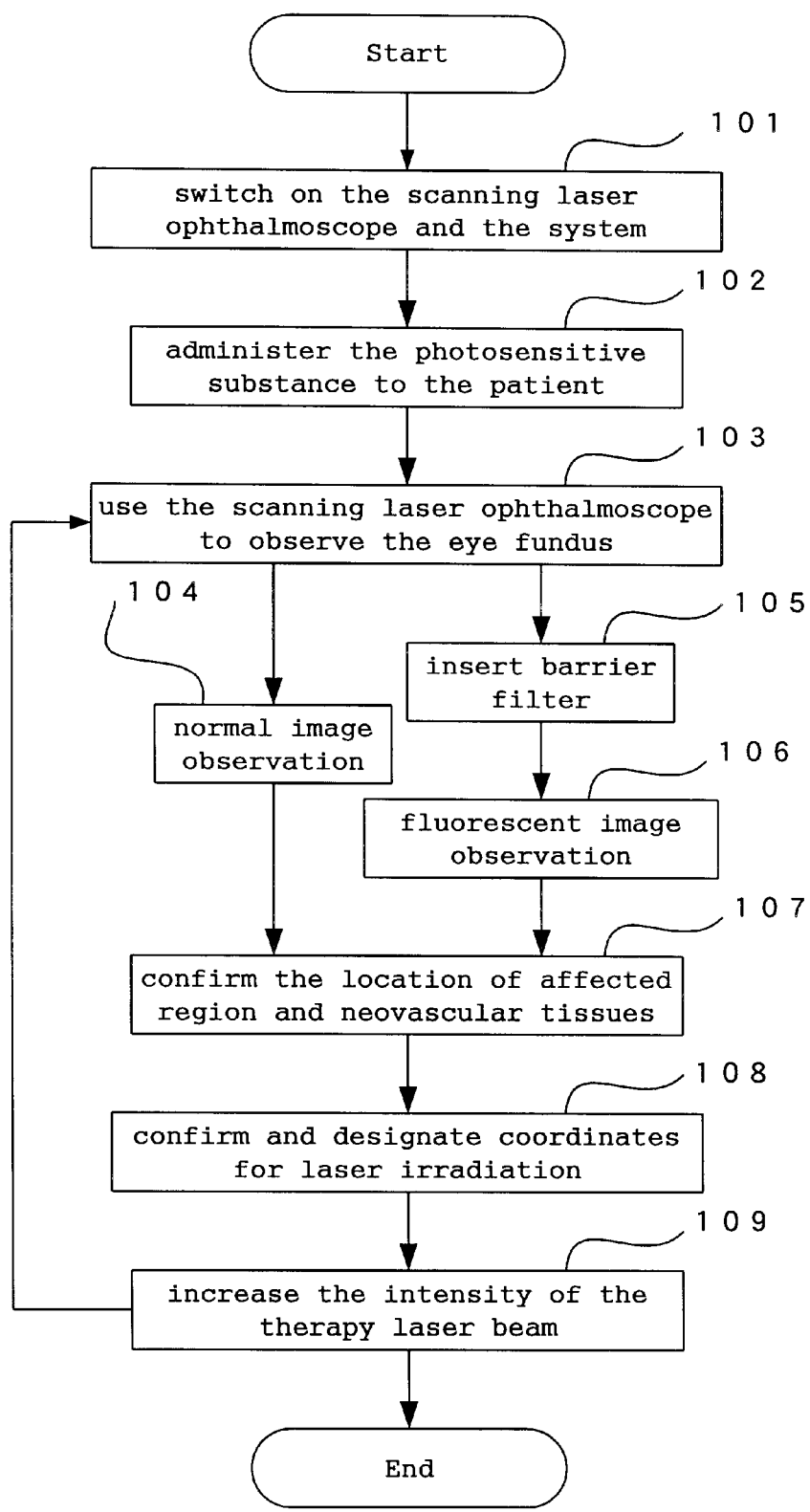
FIG. 4 is a flow chart illustrating the ophthalmic treatment procedure.

FIG. 4 is a flow chart of the procedures to treat the neovascular tissue lesion using the ophthalmic treatment apparatus. In step 101 the electric power is switched on for the scanning laser ophthalmoscope section (b), the therapy laser light source section (a) and the peripherals of section (c) such as the TV monitor and VCR.

In step 102 the photosensitive substance is administered to the patient and in step 103 the scanning laser ophthalmoscope is used to observe the eye fundus. If necessary, the fundus can be viewed as a reflex light image (step 104) or a barrier filter can be inserted and the fundus observed as a fluorescent image (steps 105 and 106). In step 107, the affected region (neovascular tissue location 34) is confirmed and the scanning region 35 to be irradiated by the high-power laser is taken into account.

In step 108 the location to be treated by laser irradiation is defined and its coordinates are designated referring to the screen image shown on the monitor 26 of the scanning laser ophthalmoscope. The region 35 with the neovascular tissues can be designated by using a mouse or other such input device 30. This enables the region to be designated on the close-up image of the fundus shown on the monitor.

In step 109 the intensity of the laser beam irradiation is increased. This is done as follows: the driver 28 is activated via the therapy laser controller 29 to operate the light modulator 2 so as to intensify the laser beam from the laser light source 1 at the time when the optical deflector 8 and galvanomirror 13 are deflecting the laser beam to scan the designated region 35.

This makes it possible for the specified part of the eye fundus to be irradiated with good precision, so that the treatment can be completed in one session. If necessary, the procedure of steps 101 to 109 can be repeated to implement the treatment a part at a time. This is indicated by the reversion from step 109 to step 103.

While the above-described embodiment has been described with reference to the use of the two laser light sources 1 and 5, the laser light source 5 can be omitted. In this case, up to the diagnosis and designation of the affected region 35, and also after the designation of the region, a weakly modulated laser beam is used except when the region is treated by irradiation. When, on the other hand, the region 35 is to be treated by irradiation, the intensity of the laser beam is increased to the treatment level.

Also, while the above description was made with reference to the embodiment in which, when the affected region is treated by laser beam irradiation, the laser beam deflection is made in the same way as it is done in the observation of the diagnostic image, the affected region 35 can be more effectively treated by, for example, making the deflector scanning angle variable. The scanning angle by the optical deflector 8 and galvanomirror 13 could, for example, be decreased, to effect concentrated microscanning of the affected region 35.

It is to be understood that the present invention is not limited to the embodiments, examples and versions described in the foregoing, and that the invention encompasses modifications to the design and implementation thereof to the extent that such modifications or changes do not depart from the gist of the invention set forth in the claims.

As described in the foregoing, in accordance with this invention, a low intensity laser beam is used to scan the eye fundus to pick up its reflection or fluorescence, thereby enabling close-up images of the eye fundus to be observed in real-time at high resolution. In particular, the fluorescent detection using a laser scanning optical system after administration of a photosensitive substance to the patient makes it possible to observe very high contrast eye fundus images, and enables reliable diagnosis of the affected regions including neovascular tissues.

The intensity of the laser beam can be increased at the affected region, so that the photochemical reaction takes place between the laser light and the photosensitive substance that accumulates specifically in the neovascular tissues to thereby destroy or seal off just the neovascular tissues, minimizing the influence on normal cells and the degradation in visual function. This thus provides an effective and reliable treatment against affections without troubles of after-effects caused by the laser therapy. In this respect, the ophthalmic treatment apparatus according to the invention is epoch-making and provides good news to patients having neovascular tissue lesion in the eye fundus.

What is claimed is:

1. An ophthalmic treatment apparatus comprising:
a laser light source for generating a first laser beam having a given intensity;
optical scanning means for deflecting the first laser beam from the laser light source at a predetermined frequency to scan with a variable scanning angle an eye fundus of a patient's eye into which a photosensitive substance that accumulates specifically in neovascular tissues of the eye fundus to be treated has been administered;
output means for detecting an intensity of reflected light and fluorescent light from the eye fundus and outputting an image of the eye fundus in accordance with the scanning by the optical scanning means;
means for defining a given region of the eye fundus containing the neovascular tissues to be treated in accordance with the outputted image of the eye fundus; and
control means for controlling the laser light source to generate a second laser beam having an intensity greater than that of the given intensity and to irradiate the second laser beam in the given region of the eye fundus to cause a photochemical reaction between the second laser beam and the photosensitive substance and thereby destroy or seal off the neovascular tissues.

2. An ophthalmic treatment apparatus according to claim 1; wherein the laser light source comprises a single laser light system.

3. An ophthalmic treatment apparatus according to claim 1; wherein the photosensitive substance comprises an oncotropic porphyrin-based chemical substance.

4. An ophthalmic treatment apparatus according to claim 1; wherein the optical scanning means includes means for scanning the eye fundus with a decreasing variable scanning angle.

5. An ophthalmic treatment apparatus according to claim 1; wherein the laser light source comprises a low-power laser light system for generating the first laser beam and a high-power laser light system for generating the second laser beam.

6. An ophthalmic treatment apparatus according to claim 5; wherein the photosensitive substance comprises an oncotropic porphyrin-based chemical substance.

7. An ophthalmic treatment apparatus comprising:
a laser light source for generating a first laser beam having a given intensity;
optical scanning means for deflecting the first laser beam from the laser light source at a predetermined frequency to scan with a variable scanning angle an eye fundus of a patient's eye into which a photosensitive substance that accumulates specifically in neovascular tissues of the eye fundus to be treated has been administered;
output means for detecting an intensity of reflected light and fluorescent light from the eye fundus and outputting an image of the eye fundus in accordance with the scanning by the optical scanning means;
setting means for setting position coordinates corresponding to a location of a given region of the eye fundus containing the neovascular tissues to be treated in accordance with the outputted image of the eye fundus; and
control means for controlling the laser light source to generate a second laser beam having an intensity greater than that of the given intensity and to irradiate the second laser beam in the given region of the eye fundus in accordance with the position coordinates to cause a photochemical reaction between the second laser beam and the photosensitive substance and thereby destroy or seal off the neovascular tissues.

8. An ophthalmic treatment apparatus according to claim 7; wherein the optical scanning means includes means for scanning the eye fundus two-dimensionally with the first laser beam.

9. An ophthalmic treatment apparatus according to claim 7; wherein the photosensitive substance comprises an oncotropic porphyrin-based chemical substance.

10. An ophthalmic treatment apparatus according to claim 7; wherein the optical scanning means includes means for scanning the eye fundus with a decreasing variable scanning angle.

11. An ophthalmic treatment apparatus according to claim 1; wherein the laser light source comprises a low-power laser light system for generating the first laser beam and a high-power laser light system for generating the second laser beam.

12. An ophthalmic treatment apparatus according to claim 11; wherein the photosensitive substance comprises an oncotropic porphyrin-based chemical substance.

13. An ophthalmic treatment apparatus comprising: a first laser light source for generating a laser beam having a given wavelength; optical scanning means for deflecting the laser beam from the first laser light source at a predetermined frequency to scan with a variable scanning angle an eye fundus of a patient's eye into which a photosensitive substance that accumulates specifically in neovascular tissues of the eye fundus to be treated has been administered; output means for detecting an intensity of reflected light and fluorescent light from the eye fundus and outputting an image of the eye fundus in accordance with the scanning by the optical scanning means; setting means for setting position coordinates corresponding to a location of a given region of the eye fundus containing the neovascular tissues to be treated in accordance with the outputted image of the eye fundus; a second light source for irradiating a laser beam in the given region of the eye fundus in accordance with the position coordinates; and means for amplifying an intensity of the laser beam irradiated in the given region of the eye fundus to cause a photochemical reaction between the laser beam and the photosensitive substance and thereby destroy or seal off the neovascular tissues.

14. An ophthalmic treatment apparatus according to claim 13; wherein the photosensitive substance comprises an oncotropic porphyrin-based chemical substance.

15. An ophthalmic treatment apparatus according to claim 13; wherein the optical scanning means includes means for scanning the eye fundus with a decreasing variable scanning angle.

16. An ophthalmic treatment apparatus according to claim 13; wherein the laser beam generated by the first light source and the laser beam irradiated by the second light source have different wavelengths.

17. An ophthalmic treatment apparatus according to claim 16; wherein the photosensitive substance comprises an oncotropic porphyrin-based chemical substance.

18. An ophthalmic treatment apparatus comprising: a first laser light source for generating a laser beam having a given wavelength; optical scanning means for deflecting the laser beam from the first laser light source at a predetermined frequency to scan with a variable scanning angle an eye fundus of a patient's eye into which a photosensitive substance that accumulates specifically in neovascular tissues of the eye fundus to be treated has been administered; detecting means for detecting an intensity of reflected light and fluorescent light from the eye fundus resulting from the scanning by the optical scanning means; output means for outputting an image of the eye fundus in accordance with the intensity of reflected light and fluorescent light from the eye fundus detected; setting means for setting position coordinates corresponding to a location of a given region of the eye fundus containing the neovascular tissues to be treated in accordance with the outputted image of the eye fundus; a second light source for irradiating a laser beam having a given wavelength in the given region of the eye fundus in accordance with the position coordinates; and means for amplifying an intensity of the laser beam irradiated in the given region of the eye fundus to cause a photochemical reaction between the laser beam and the photosensitive substance and thereby destroy or seal off the neovascular tissues.

19. An ophthalmic treatment apparatus according to claim 18; wherein the photosensitive substance comprises an oncotropic porphyrin-based chemical substance.

20. An ophthalmic treatment apparatus according to claim 18; wherein the optical scanning means includes means for scanning the eye fundus with a decreasing variable scanning angle.

21. An ophthalmic treatment apparatus according to claim 18; wherein the wavelength of the second laser light source is equal to or shorter than that of the first light source.

22. An ophthalmic treatment apparatus according to claim 21; wherein the photosensitive substance comprises an oncotropic porphyrin-based chemical substance.

23. An ophthalmic treatment apparatus according to claim 18; wherein the detecting means comprises a barrier filter for blocking light of a given wavelength from the beam of light emitted by the second light source.

24. An ophthalmic treatment apparatus according to claim 23; wherein the photosensitive substance comprises an oncotropic porphyrin-based chemical substance.

25. An ophthalmic treatment method, comprising the steps of: administering into an eye fundus of a patient's eye a photosensitive substance that accumulates specifically in neovascular tissues of the eye fundus to be treated; scanning the eye fundus with a variable scanning angle using a first laser beam at a predetermined frequency; detecting an intensity of reflected light and fluorescent light from the eye fundus in accordance with the scanning of the eye fundus; generating an image of the eye fundus in accordance with the detected intensity of reflected light and fluorescent light; identifying a location of the eye fundus containing the neovascular tissues to be treated in accordance with the generated image of the eye fundus and storing position coordinates corresponding to the identified location; and scanning the location of the eye fundus corresponding to the position coordinates with a variable scanning angle using a second laser beam to cause a photochemical reaction between the second laser beam and the photosensitive substance and thereby destroy or seal off the neovascular tissues.

26. An ophthalmic treatment method according to claim 25; further comprising the step of amplifying an intensity of the second laser beam during scanning of the location of the eye fundus corresponding to the position coordinates.

27. An ophthalmic treatment method according to claim 25; wherein the generating step comprises generating a fluorescent image of the eye fundus; and wherein the identifying step comprises identifying the location of the eye fundus in accordance with the generated fluorescent image of the eye fundus.

28. An ophthalmic treatment method according to claim 25; wherein each of the scanning steps comprises scanning the eye fundus and the location of the eye fundus corresponding to the position coordinates, respectively, with a decreasing variable scanning angle.

29. An ophthalmic treatment method according to claim 25; further comprising the steps of scanning the eye fundus with the first laser beam using a first laser light source and scanning the eye fundus with the second laser beam using a second laser light source.

30. An ophthalmic treatment method according to claim 29; wherein the generating step comprises generating a fluorescent image of the eye fundus; and wherein the identifying step comprises identifying the location of the eye fundus in accordance with the generated fluorescent image of the eye fundus.

* * * * *